(12) United States Patent
Kondoh et al.

(10) Patent No.: US 6,184,383 B1
(45) Date of Patent: Feb. 6, 2001

(54) METHOD OF PRODUCING ACETALS

(75) Inventors: Atsuo Kondoh; Fumio Iwamoto, both of Odawara (JP)

(73) Assignee: Fuji Photo Film Co., Ltd., Kanagawa (JP)

( * ) Notice: Under 35 U.S.C. 154(b), the term of this patent shall be extended for 0 days.

(21) Appl. No.: 09/442,505

(22) Filed: Nov. 18, 1999

(30) Foreign Application Priority Data

Nov. 20, 1998 (JP) .................................................. 10-331674

(51) Int. Cl.$^7$ ...................... C07D 211/72; C07D 285/12; C07D 271/10; C07D 257/00
(52) U.S. Cl. .......................... 546/298; 548/142; 548/144; 548/251
(58) Field of Search .............................. 546/298; 548/142, 548/144, 251

(56) References Cited

U.S. PATENT DOCUMENTS 5,633,264 * 5/1997 Domagala et al. .................. 514/312

* cited by examiner

*Primary Examiner*—Joseph McKane
*Assistant Examiner*—Joseph Murray
(74) *Attorney, Agent, or Firm*—Birch, Stewart, Kolasch & Birch, LLP

(57) ABSTRACT

There is disclosed a method of producing acetals, which comprises reacting a compound of formula (I), at least one compound selected from a group consisting of a compound of formula (II), paraformaldehyde, and trioxane; and a compound of formula (III), to synthesize an acetal of formula (IV), wherein the reaction is carried out in the presence of an oxidizing agent and an acid:

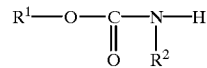

formula (I)

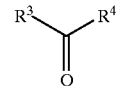

formula (II)

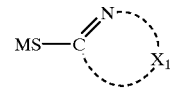

formula (III)

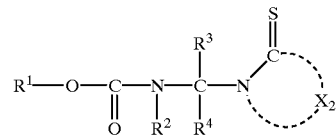

formula (IV)

wherein $R^1$ is an alkyl group etc., $R^2$ is an alkyl or aryl group, $R^3$ and $R^4$ each independently are a hydrogen atom, an alkyl group or an aryl group, $X_1$ and $X_2$ each are a group of nonmetal atoms necessary to form a 5- or 6-membered N-containing heterloring, and M is a hydrogen atom or a cation. This method can give acetal compounds with good efficiency and a high yield.

9 Claims, No Drawings

METHOD OF PRODUCING ACETALS

FIELD OF THE INVENTION

The present invention relates to a method of producing a compound having an acetal skeleton, with good efficiency and a high yield. The compound is useful for a photographic coupler, or as an intermediate in a variety of organic synthesis.

BACKGROUND OF THE INVENTION

Hitherto, synthesis of acetals having the structure shown below has not been sufficiently studied. One general method therefor is described in JP-A-5-313322 ("JP-A" means an unexamined published Japanese patent application).

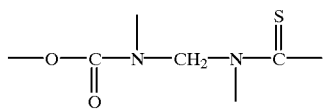

Specifically, as shown in scheme (I) below, it was a method wherein (A) was subjected to methylolation with paraformaldehyde, to synthesize (B), and the resultant (B) was reacted with mercapto azole in the presence of zinc iodide, to obtain (C) as an objective product.

Scheme (I)

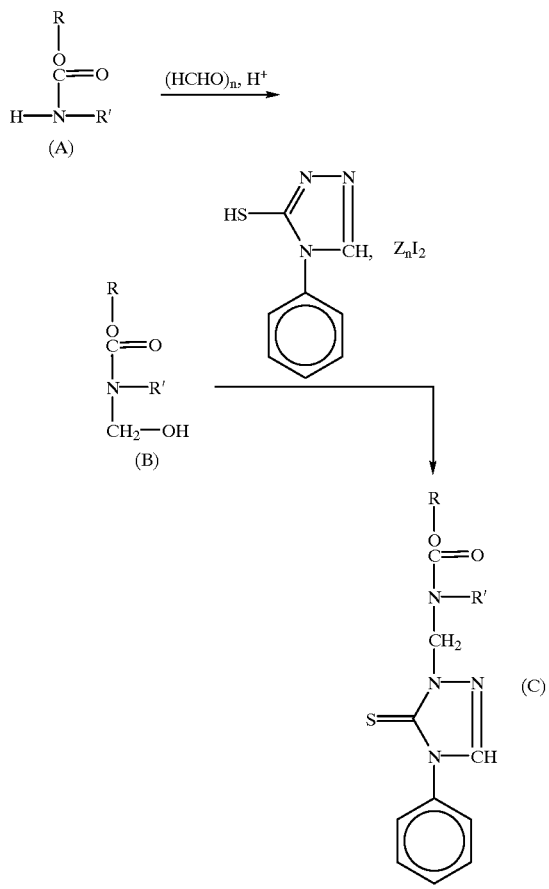

However, the above-described method had such problems that
(i) Two steps are necessary to obtain the object,
(ii) The yield is low in each of the steps,
(iii) It is extremely difficult to isolate (B) using a means other than column purification, because (B) of an intermediate is synthesized with a low yield and poor crystallinity,
(iv) Paraformaldehyde is adhered onto a cooling tube during the synthesis of (B), and
(v) Unless the purity of (B) is increased, the synthesis reaction of (C) does not go well.

Compared to such a conventional method, JP-A-5-331145 describes a method in which a reaction is efficiently carried out using a metal salt, whose typical example is copper bromide, as a catalyst. However, this method still has such problems that (1) The yield is not satisfactory, and
(2) It causes a heavy load on environment, at the dealing and disposal of metal salt (heavy metal) used as a catalyst.

SUMMARY OF THE INVENTION

An object of the present invention is to provide a method of producing acetal compounds, with good efficiency and high yield, which method improves the above-mentioned drawbacks of the conventional methods.

Other and further objects, features, and advantages of the invention will appear more fully from the following description.

DETAILED DESCRIPTION OF THE INVENTION

The above-described object of the present invention has been accomplished by (1) A method of producing acetals, comprising reacting a compound represented by formula (I), at least one compound selected from a group consisting of a compound represented by formula (II), paraformaldehyde, and trioxane; and a compound represented by formula (III), to synthesize an acetal represented by formula (IV), wherein the reaction is carried out in the presence of an oxidizing agent and an acid;

formula (I)

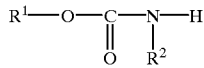

wherein $R^1$ represents an alkyl group, an aryl group, or a heterocyclic group; and $R^2$ represents an alkyl group or an aryl group;

formula (II)

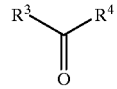

wherein $R^3$ and $R^4$ each independently represent a hydrogen atom, an alkyl group, an alkenyl group, an alkynyl group, an alkoxycarbonyl group, an aryloxycarbonyl group, a carbamoyl group, a sulfamoyl group, an aryl group, or a heterocyclic group;

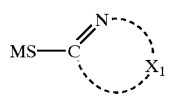

formula (III)

wherein $X_1$ represents a group of non-metal atoms necessary to form a 5- or 6-membered nitrogen-containing heterocycle; and M represents a hydrogen atom or a cation (e.g. sodium ion);

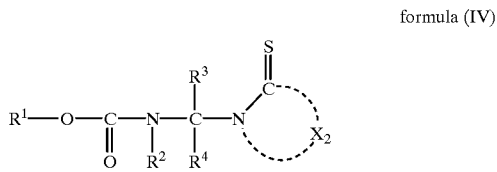

formula (IV)

wherein $R^1$, $R^2$, $R^3$, and $R^4$ each have the same meanings as in formulae (I) and (II), and $X_2$ represents the same group of atoms as $X_1$ in formula (III).

As preferable embodiments of the present invention, the following methods can be mentioned:

(2) The method of producing acetals as stated in the above (1), wherein $R^1$ is represented by formula (VI):

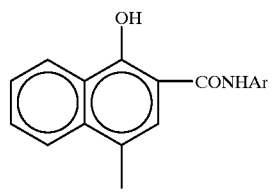

formula (VI)

wherein Ar represents a substituted or unsubstituted alkyl group or aryl group;

(3) The method of producing acetals as stated in the above (1), wherein the oxidizing agent is a peroxide; and (4) The method of producing acetals as stated in the above (1), wherein the oxidizing agent is a hydrogen peroxide, or an addition product thereof.

Compounds represented by formula (I) are explained below. $R^1$ represents an alkyl group, (e.g. methyl, tert-butyl, 2-ethylhexyl, decyl, octadecyl, benzyl), an aryl group (e.g. phenyl, 1-naphthyl, 2-naphthyl), or a heterocyclic group (e.g. 3-pyridyl, 2-thienyl, 1-methyl-3-indolyl). Further, these groups may have a substituent. Examples of the substituent include a hydroxyl group, a carbamoyl group (e.g. carbamoyl, dimethylcarbamoyl, propylcarbamoyl, octadecylcarbamoyl, morpholinocarbonyl), an alkoxy group (e.g. methoxy, tert-butoxy, tetradecyloxy), an aryloxy group (e.g. phenoxy, 2-naphthoxy), an alkylthio group (e.g. methylthio, isopropylthio, decylthio), an arylthio group (e.g. phenylthio, 1-naphthylthio), an alkoxycarbonyl group (e.g. methoxycarbonyl, 2-ethylhexyloxycarbonyl, 2-hexyldecyloxycarbonyl, isopropyloxycarbonyl), an aryloxycarbonyl (e.g. phenoxycarbonyl), an acyl group (e.g. acetyl, pivaloyl, benzoyl), a sulfonyl group (e.g. methanesulfonyl, p-toluenesulfonyl), a nitro group, a cyano group, a halogen atom (e.g. fluoro, chloro, bromo), a sulfamoyl group, an acylamino group (e.g. acetylamino, butanoylamino, benzoylamino), a sulfonylamino group, and other amino groups (e.g. dimethylamino). Further, these groups may be further substituted.

$R^2$ represents a substituted or unsubstituted alkyl group (e.g. methyl, isopropyl, ethyl, hexyl, tetradecyl, benzyl) or aryl group (e.g. phenyl, 1-naphthyl, 2-naphthyl).

Examples of the substituent that $R^2$ may have are the same as those mentioned as substituents for $R^1$.

Next, compounds represented by formula (II) are explained below.

$R^3$ and $R^4$ each independently represent a hydrogen atom, an alkyl group, an alkenyl group, an alkynyl group, an alkoxycarbonyl group, an aryloxycarbonyl group, a carbamoyl group, a sulfamoyl group, an aryl group, or a heterocyclic group. Examples of the aryl group include a phenyl group and a naphthyl group. Examples of the heterocyclic group include a 2-furyl group or a 2-thienyl group. Further, specific examples of other groups besides these groups are those mentioned for $R^1$. When $R^3$ or $R^4$ represents a group other than a hydrogen atom, the group may further have a substituent.

Preferably $R^3$ and $R^4$ each represent a hydrogen atom, an alkyl group having 1 to 6 carbon atoms, or a phenyl group. More preferably, at least one of $R^3$ and $R^4$ represents a hydrogen atom. Particularly preferably, both $R^3$ and $R^4$ represent a hydrogen atom.

Next, compounds represented by formula (III) are explained below.

$X_1$ represents a group of non-metal atoms necessary to form a 5- or 6-membered nitrogen-containing heterocycle, which may be further condensed with another ring. Further, the nitrogen-containing heterocycle or the condensed ring may have a substituent thereon.

A structure of the nitrogen-containing heterocycle moiety having a mercapto group of the compound represented by formula (III) is preferably represented by formulae (III-1) to (III-8), as shown below. Each bond on the heterocycle of formulae (III-1) to (III-8) represent a bonding site with a hydrogen atom or a substituent.

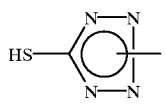

(III-1)

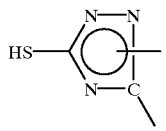

(III-2)

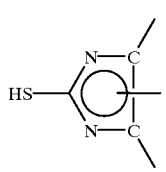

(III-3)

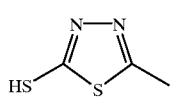

(III-4)

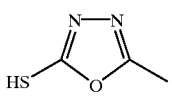 (III-5)

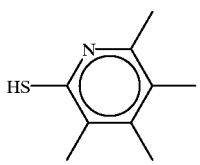 (III-6)

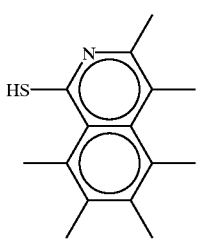 (III-7)

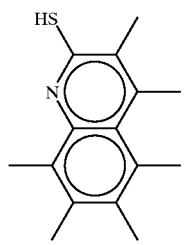 (III-8)

Among these, (III-1), (III-2), (III-4), (III-5), and (III-6) are preferable, and (III-1) and (III-4) are particularly preferable.

Examples of the substituent include not only those mentioned as substituents for $R^1$, but also an alkyl group (e.g. ethyl, butyl, tert-butyl, benzyl) and an aryl group (e.g. phenyl). Further, these groups may further have a substituent. Preferably, the substituent is an alkyl group, an aryl group, an alkylthio group, an alkoxycarbonyl group, or an aryloxycarbonyl group.

Further, when $R^1$ of the compounds each represented by formula (I) or (IV) is a group represented by formula (VI) shown below, Ar in formula (VI) represents a substituted or unsubstituted alkyl or aryl group.

formula (VI)

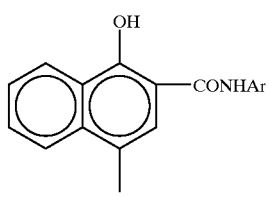

When Ar represents an alkyl group, specific examples thereof include, for example, methyl, propyl, butyl, decyl, 2-hexyldecyl, octadecyl, isobutyl, and 1,1-dimethylpropyl, which may further have a substituent. Further, when Ar represents an aryl group, specific examples thereof include, for example, phenyl, 1-naphthyl, and 2-naphthyl, which may further have a substituent. When a group represented by Ar has a substituent, specific examples thereof are the substituents mentioned for $R^1$.

The reaction according to the present invention is carried out in the presence of both an oxidizing agent and an acid.

Examples of the oxidizing agent that can be used include an aqueous solution of hydrogen peroxide, sodium percarbonate ($2Na_2CO_3 \cdot 3H_2O_2$), manganeses ($KMnO_4$, $MnO_2$), halogens ($I_2$, $Br_2$, $Cl_2$), quinones (chloranil, orthochloranil, DDQ, etc.), dimethylsulfoxide, perchlorates ($NaClO_4$, $NaClO_3$, $KClO_3$, etc.), and periodates ($NaIO_4$, $KIO_3$, $H_5IO_6$, etc.), and N-halocarboxylic acid amides (N-chlorosuccinimide, N-bromosuccinimide, 1,3-dichloro-5,5-dimethylhydantoin, 1,3-dibromo-5,5-dimethylhydantoin, N-bromophthalimide, etc.). Preferred oxidizing agents are an aqueous solution of hydrogen peroxide, sodium percarbonate, halogens, perchlorates, and periodates, each of which can be easily discharged into an aqueous layer by washing. Particularly preferred, of these compounds, are an aqueous solution of hydrogen peroxide and sodium percarbonate, because they prevent the waste water of reaction from including halogens.

Preferred acids that can be used are proton acids, such as hydrochloric acid, hydrobromic acid, sulfuric acid, and formic acid. of these acids, hydrobromic acid is particularly preferred, in view of reaction selectivity.

The molar ratio of the compounds in the reaction is not limited in particular. Each of the compound represented by formula (I); the compound represented by formula (II), paraformaldehyde, or trioxane; and the compound represented by formula (III), may be used in an equimolar amount. Further, in order to accelerate a reaction, any of these compounds may be used in an excess amount. In this case, the excess amount is preferably within 10 times the least amount among the three compounds, and more preferably within 2 times.

Further, in order to suppress side reaction, each of the compounds represented by formulae (II) and (III) is preferably used in a molar amount of 1.1 to 2.0 times, more preferably 1.2 to 1.6 times, and particularly preferably 1.4 times, that of the compound represented by formula (I).

The oxidizing agent can be used in an amount 0.001 times to 10 times the number of moles of the compound represented by formula (I). Within the range, preferable amount is in the range of 0.05 times to 0.5 times. A particularly preferable amount is in the range of 0.2 to 0.3, in view of cost merits and environment.

The acid can be used in an amount 0.1 to 10 times the number of moles of the compound represented by formula (I). Within the range, preferable amount is in the range of 0.5 times to 5 times. Particularly preferably, the amount is in the range of 1 time to 2 times in view of cost merits and environment.

The reaction can be carried out in the range of 0° C. to 150° C., preferably from 15° C. to 100° C., and particularly preferably from 20° C. to 80° C.

A variety of reaction solvents can be used. Of these solvents, preferred are hydrocarbon-series solvents (e.g. benzene, toluene, hexane), halogen-series solvents (e.g. methylene chloride, chloroform, chlorobenzene, 1,2-dichloroethane), ether-series solvents (e.g. tetrahydrofuran, anisole), and aprotic polar solvents (e.g. acetonitrile, nitromethane, dimethylsulfoxide, N,N'-dimethylimidazolidinone, N,N-dimethylformamide). Further, a plurality of solvents may be used in a mixture, or alternatively the reaction may be carried out in the absence of a solvent. When a solvent is used, hydrocarbon-series solvents (e.g. benzene, toluene, hexane) and halogen-series solvents (e.g. methylene chloride, chloroform, chlorobenzene, 1,2-dichloroethane) are preferred, in viewpoints of reactivity and suppression of by-products.

Of these, toluene, hexane, and a mixture thereof are particularly preferred. The mixing ratio by volume of toluene/hexane is preferably 1/1 to 1/4, and most preferably 1/3. When the reaction is carried out using a solvent, with respect to the compound represented by formula (I); the compound represented by formula (II), paraformaldehyde, or trioxane; and the compound represented by formula (III), the concentration of the compound having the least number of moles among the three kinds of compounds is preferably $10^{-2}$ to 10 M, more preferably $10^{-1}$ to 5 M, and particularly preferably 0.3 to 1 M, with the proviso that paraformaldehyde is calculated in terms of HCHO.

The time period of reaction to be carried out may be in the range of 30 minutes to 3 days, and it varies widely depending on the properties of reaction substrates. Generally, the reaction is carried out in the range of 1 hour to 15 hours, and preferably in the range of 2 hours to 10 hours.

As a post-treatment of the reaction, after completion of the reaction, a reaction solution can be washed, and then the resulting organic layer can be concentrated. An object can be frequently isolated by adding a suitable solvent into the thus-obtained residue. Further, alternatively the residue obtained by concentrating the organic layer can be purified by usual treatment methods, such as distillation, and a column purification using a silica gel or the like.

Specific examples of the compound represented by formula (IV) and the compound having a group represented by formula (VI) are shown below, but the present invention is not limited to them.

TABLE 1

$$R^1-O-\underset{\underset{O}{\parallel}}{C}-\underset{\underset{R^2}{\mid}}{N}-\underset{\underset{R^4}{\mid}}{\overset{\overset{R^3}{\mid}}{C}}-Ar_2$$

| Compound No. | $R^1$ | $R^2$ | $R^3$ | $R^4$ | $Ar_2$ |
|---|---|---|---|---|---|
| IV-1 | —C₆H₅ (phenyl) | —C₆H₅ (phenyl) | H | H | 1-methyl-4-phenyl-5-thio-tetrazole |
| IV-2 | —C₆H₅ (phenyl) | —CH₂—C₆H₅ | " | " | " |
| IV-3 | —C₆H₅ (phenyl) | —C₆H₁₃ | " | " | " |
| IV-4 | —C₂H₅ | —C₆H₅ (phenyl) | " | " | " |
| IV-5 | —C₆H₅ (phenyl) | —CH₂—C₆H₅ | " | " | 1-methyl-4-butyl-5-thio-tetrazole |
| IV-6 | " | —C₆H₁₃ | " | " | " |

TABLE 1-continued $$R^1-O-\underset{\underset{O}{\|}}{C}-\underset{R^2}{N}-\underset{R^4}{\overset{R^3}{C}}-Ar_2$$

| Compound No. | R¹ | R² | R³ | R⁴ | Ar₂ |
|---|---|---|---|---|---|
| IV-5 | C₆H₅-CH₂— | cyclohexyl | H | H | 1-methyl-4-phenyl-5-thio-1,2,4-triazole (N-CH ring with N-CH₃, N-C₆H₅, C=S) |
| IV-6 | " | —CHCO₂C₂H₅<br>      \|<br>      CH₃ | H | H | 1-methyl-4-(CH₂CO₂C₃H₇)-5-thio-tetrazole |
| IV-7 | " | —CH₂CO₂C₂H₅ | H | H | 1-methyl-4-C₄H₉-5-thio-tetrazole |
| IV-8 | CH₃O-C₆H₄-CH₂— | —CH₂CH₂F | H | H | 3-methyl-5-(SCH₃)-2-thio-1,3,4-oxadiazole |

TABLE 2

[Structure: 1-hydroxy-naphthalene with 2-CONH-Ar₁ and 4-O-C(=O)-N(R²)-C(R³)(R⁴)-Ar₂ substituents]

| Compound No. | Ar₁ | R² | R³ | R⁴ | Ar₂ |
|---|---|---|---|---|---|
| VI-1 | 2-methyl-6-(OC₁₄H₂₉)phenyl | —CH(CH₃)₂ | H | H | 1-methyl-4-phenyl-tetrazole-5-thione |
| VI-2 | " | " | " | " | 1-methyl-4-butyl-tetrazole-5-thione |
| VI-3 | " | " | " | " | 4-methyl-5-(methylthio)-1,3,4-thiadiazole-2-thione |
| VI-4 | " | " | " | " | 1-methyl-pyridine-2-thione |
| VI-5 | " | phenyl | " | " | 1-methyl-4-phenyl-tetrazole-5-thione |

TABLE 2-continued

[Structure: 1-hydroxy-naphthalene with 2-CONH-Ar₁ and 4-O-C(=O)-N(R²)-C(R³)(R⁴)-Ar₂]

| Compound No. | Ar₁ | R² | R³ | R⁴ | Ar₂ |
|---|---|---|---|---|---|
| VI-6 | 2-methyl-3-OC₁₄H₂₉-phenyl | 4-methoxyphenyl (via CH₂, p-OCH₃ tolyl) | H | H | 1-methyl-4-phenyl-tetrazole-5-thione |
| VI-7 | " | —CH₂CO₂CH₃ | " | " | 1-methyl-4-C₄H₉-tetrazole-5-thione |
| VI-8 | " | —CH₂CH₂Cl | " | " | 1-methyl-4-phenyl-tetrazole-5-thione |
| VI-9 | 3-methyl-2-OC₁₀H₂₁-naphthyl | —CH₂CO₂C₂H₅ | " | " | 3-methyl-5-(SCH₃)-1,3,4-oxadiazole-2-thione |
| VI-10 | —(CH₂)₃OC₁₂H₂₅ | " | " | " | " |
| VI-11 | —(CH₂)₃—O—(3,5-di-tert-C₅H₁₁-phenyl) | " | " | " | " |

TABLE 2-continued
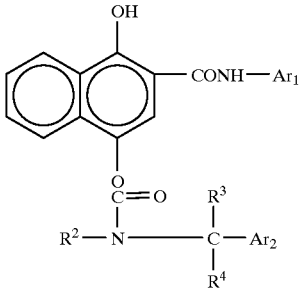
| Compound No. | Ar$_1$ | R$^2$ | R$^3$ | R$^4$ | Ar$_2$ |
|---|---|---|---|---|---|
| VI-12 | —C$_{12}$H$_{25}$ | —CH(CH$_3$)$_2$ | H | H | 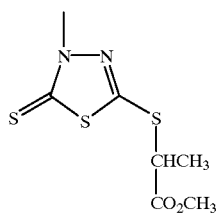 |
| VI-13 | 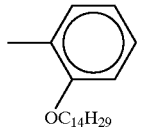 | " | H | —CO$_2$CH$_3$ | 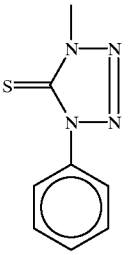 |
| VI-14 | " | —CH$_2$CH$_2$Cl | H | H | 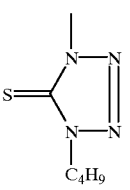 |
| VI-15 | " | " | 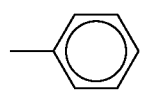 | H | " |
| VI-16 | " | " | —CH$_3$ | —CH$_3$ | " |
| VI-17 | " | —CH$_2$CO$_2$C$_2$H$_5$ | H | H | 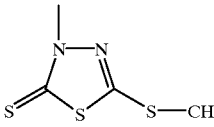 |

TABLE 2-continued

[Structure shown at top of table: naphthalene with OH, CONH-Ar₁, and O-C(=O)-N(R²)-C(R³)(R⁴)-Ar₂ substituents]

| Compound No. | Ar₁ | R² | R³ | R⁴ | Ar₂ |
|---|---|---|---|---|---|
| VI-18 | " | —CH₂CO₂CH₃ | " | " | [1-methyl-4-phenyl-tetrazoline-5-thione structure] |

EXAMPLES

Example 1

Synthesis of Exemplified Compound (VI-7) (use of a 35% Hydrogen Peroxide Aqueous Solution)

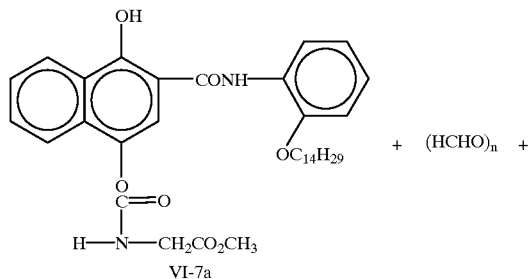

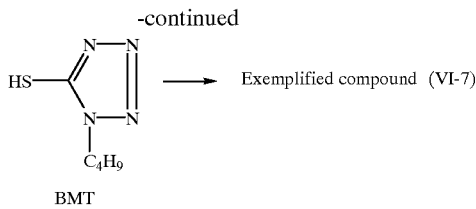

A mixture of VI-7a (0.1 mol), paraformaldehyde (0.14 mol in terms of HCHO, hereinafter expressed likewise), BMT (0.14 mol), 2.4 g of a 35% hydrogen peroxide aqueous solution (25 mmol in terms of $H_2O_2$), 27 g of a 47% HBr aqueous solution (0.16 mol in terms of HBr), 65 ml of toluene, and 180 ml of normal hexane, was allowed to react at 50° C. for 8 hours. Thereafter, 60 ml of normal hexane and 280 ml of water were added to the reaction mixture, and it was stirred, at an inner temperature of 40° C. or more so as to prevent deposition of crystals, and then the resulting aqueous layer was separated. Further, the resulting organic layer was washed twice with 280 ml of water, at an inner temperature of 40° C. or more. 40 ml of isopropyl alcohol was added to the organic layer and cooled gradually to an inner temperature of 0° C., and deposited crystals were separated by filtration and dried, to obtain 0.09 mol of exemplified compound VI-7 (yield 90%). m.p. 67.0~69.0° C.

Example 2

Synthesis of Exemplified Compound (VI-7) (Various Kinds of Oxidizing Agents)

Reaction was carried out under the same conditions as in Example 1, except that the 35% hydrogen peroxide aqueous solution used in Example 1 was changed to one of the oxidizing agents shown in Table 3, shown below. According to the same process as in Example 1, purified exemplified compound VI-7 was obtained. The yields are shown in Table 3.

The results in Table 3 show that, when no oxidizing agent was added, the progress of reaction was extremely slow (Test No. 8), whereas the reaction was accelerated by adding various kinds of oxidizing agents, which resulted in remarkable improvement in yield (Test Nos. 1 to 7). Further, the yield was low in Test No. 9.

TABLE 3

| Test No. | Acid[1] | Oxidizing agent[1] | Yield of Exemplified compound VI-7 |
|---|---|---|---|
| 1 (This invention) | HBr (0.16 mol) | 35% $H_2O_2$ aqueous solution (25 mmol) | 90% |
| 2 (This invention) | HBr 0.16 mol | 2 $Na_2CO_3 \cdot 3H_2O_2$ 17 mmol | 90% |
| 3 (This invention) | HBr (0.16 mol) | $KMnO_4$ (25 mmol) | 91% |
| 4 This invention) | HBr (0.16 mol) | Dimethyl sulfoxide (25 mmol) | 93% |
| 5 (This invention) | HBr (0.16 mol) | $I_2$ (25 mmol) | 85% |
| 6 (This invention) | HBr (0.16 mol) | o-chloranil[2] (25 mmol) | 93% |
| 7 (This invention) | HBr (0.16 mol) | DDQ[3] (25 mmol) | 92% |
| 8 (Comparative example) | HBr (0.16 mol) | None | 70% |
| 9[4] (Comparative example) | None | $CuBr_2$ (25 mmol) | 75% |

[1] Number of mol per 0.1 mol of (VI-7a)

[2]
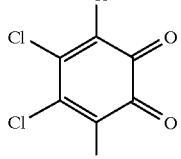

[3]
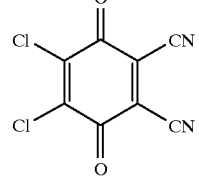

[4] Method in JP-A-5-331145

Example 3

Synthesis of Exemplified Compound (VI-18)

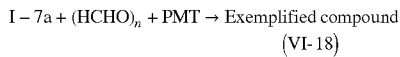

A mixture of VI-7a (0.1 mol), paraformaldehyde (0.14 mol in terms of HCHO), PMT (0.14 mol), 2.4 g of a 35% hydrogen peroxide aqueous solution (25 mmol in terms of $H_2O_2$), 27 g of a 47% HBr aqueous solution (0.16 mol in terms of HBr), 110 ml of toluene, and 150 ml of normal hexane, was allowed to react at 50° C. for 8 hours. Thereafter, 35 ml of methanol and 360 ml of water were added to the reaction mixture, and it was stirred, at an inner temperature of 40° C. or more so as to prevent deposition of crystals, and then the resulting aqueous layer was separated. Further, a process, comprising adding 360 ml of water and 35 ml of methanol to the organic layer, stirring the mixture, and then separating the aqueous layer, was repeated twice, at an inner temperature of 40° C. or more. 50 ml of isopropyl alcohol, 50 ml of methanol, 60 ml of toluene, and 370 ml of normal hexane were added to the thus obtained organic layer and cooled gradually to an inner temperature of 0° C., and deposited crystals were separated by filtration and dried, to obtain 0.09 mol of exemplified compound VI-18 (yield 90%). m.p. 77.5~79.5° C.

Example 4

Synthesis of Exemplified Compound (IV-2)

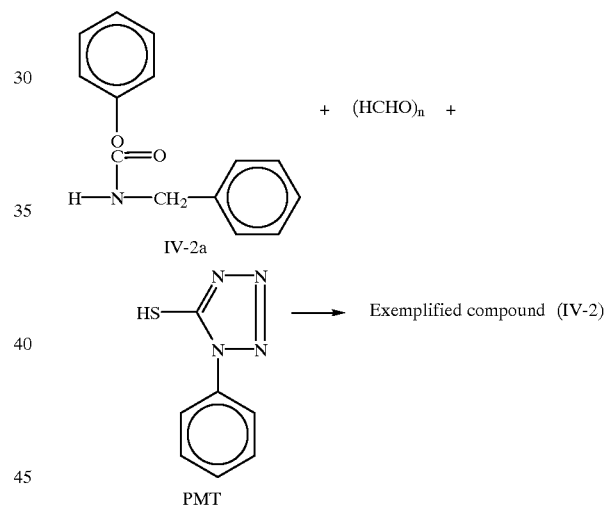

A mixture of IV-2a (13.2 mmol), paraformaldehyde (15.3 mmol), PMT (13.9 mmol), 0.35 g of $2Na_2CO_3 \cdot 3H_2O_2$, 3.6 g of a 47% HBr aqueous solution, 12 ml of toluene, and 3 ml of normal hexane, was allowed to react at 50° C. for 4 hours. Thereafter, 6 ml of normal hexane and 25 ml of water were added to the reaction mixture, and stirred, and then the aqueous layer was separated. Further, to an organic layer, 25 ml of water and 0.85 g of sodium sulfite, in order to discharge an excess amount of PMT into an aqueous layer, were added and stirred, and then the aqueous layer was separated. To the organic layer, 25 ml of water was added and stirred, and after the aqueous layer was separated, the organic layer was concentrated. The thus-obtained concentrated residue was purified by means of silica gel column chromatography (hereinafter referred to as column), to obtain 11.9 mmol (yield 90%) of exemplified compound IV-2 (oily matter).

Example 5

Synthesis of Exemplified Compound (IV-5)

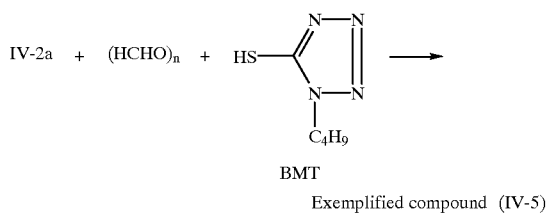

A mixture of IV-2a (13.2 mmol), paraformaldehyde (18.3 mmol), BMT (18.5 mmol), 0.35 g of $2Na_2CO_3.3H_2O_2$, 3.6 g of a 47% HBr aqueous solution, 3 ml of toluene, and 9 ml of normal hexane, was allowed to react at 50° C. for 4 hours. Thereafter, 6 ml of toluene and 20 ml of water were added to the reaction mixture, and stirred, and then the aqueous layer was separated. Further, to an organic layer, 20 ml of water and 0.85 g of sodium sulfite, in order to discharge an excess amount of BMT into an aqueous layer, were added and stirred, and then the aqueous layer was separated. To the thus-obtained organic layer, 20 ml of water was added and stirred, and after the aqueous layer was separated, the organic layer was concentrated. The thus-obtained concentrated residue was purified by means of column, to obtain 12.8 mmol (yield 97%) of exemplified compound IV-5 (oily matter).

Example 6

Synthesis of Exemplified Compound (IV-3)

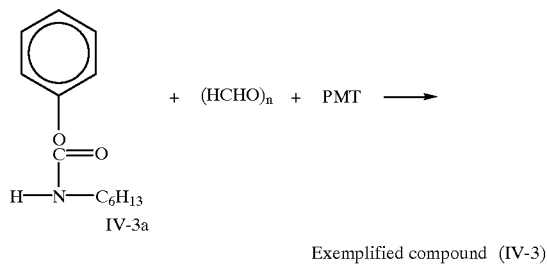

A mixture of IV-3a (13.6 mmol), paraformaldehyde (19.0 mmol), PMT (19.0 mmol), 0.35 g of $2Na_2CO_3.3H_2O_2$, 3.7 g of a 47% HBr aqueous solution, 12 ml of toluene, and 3 ml of normal hexane, was allowed to react at 50° C. for 2 hours. Thereafter, 6 ml of normal hexane and 20 ml of water were added to the reaction mixture, and stirred, and then the aqueous layer was separated. To the thus-obtained organic layer, 20 ml of warm water (40° C.) were added and stirred, and then the aqueous layer was separated. Further, to the organic layer, 20 ml of warm water (40° C.) was added and stirred, and after the aqueous layer was separated, the organic layer was concentrated. The thus-obtained concentrated residue was purified by means of column, to obtain 12.9 mmol (yield 95%) of exemplified compound IV-3 (oily matter).

Example 7

Synthesis of Exemplified Compound (IV-6)

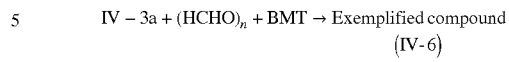

A mixture of IV-3a (13.6 mmol), paraformaldehyde (19.0 mmol), BMT (14.2 mmol), 0.35 g of $2Na_2CO_3.3H_2O_2$, 3.7 g of a 47% HBr aqueous solution, 3 ml of toluene, and 9 ml of normal hexane, was allowed to react at 50° C. for 2 hours. Thereafter, 6 ml of toluene and 20 ml of water were added to the reaction mixture, and stirred, and then the aqueous layer was separated. Further, to the thus-obtained organic layer, 20 ml of water and 0.85 g of sodium sulfite, in order to discharge an excess amount of BMT into an aqueous layer, were added and stirred, and then the aqueous layer was separated. To the organic layer, 25 ml of water was added and stirred, and after the aqueous layer was separated, the organic layer was dried with sodium sulfate and concentrated, to obtain 12.8 mmol (yield 94%) of exemplified compound IV-6 (oily matter).

Example 8

Synthesis of Exemplified Compound (VI-2)

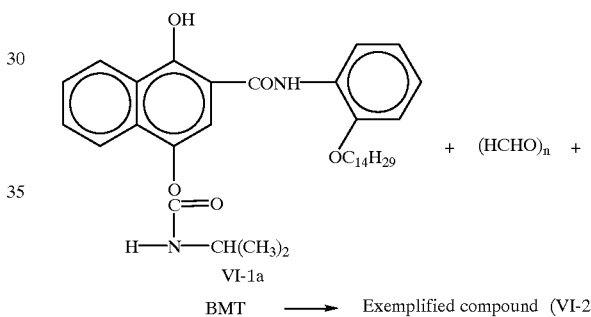

A mixture of VI-1a (5.2 mmol), paraformaldehyde (7.3 mmol), BMT (7.3 mmol), 0.14 g of $2Na_2CO_3.3H_2O_2$, 2.9 g of a 47% HBr aqueous solution, 9 ml of toluene, and 3 ml of normal hexane, was allowed to react at 50° C. for 8 hours. Thereafter, 6 ml of normal hexane and 25 ml of warm water (40° C.) were added to the reaction mixture, and then an aqueous layer was separated. Further, a process, comprising adding 25 ml of warm water (40° C.) to the organic layer, stirring the mixture, and then separating the aqueous layer, was repeated twice, and then the organic layer was concentrated. The concentrated reside was dissolved in 4 ml of isopropyl alcohol, 2 ml of ethyl acetate, and 20 ml of normal hexane, then the mixture cooled gradually to an inner temperature of 0° C., and deposited crystals were separated by filtration and dried, to obtain 4.2 mmol of exemplified compound VI-2 (yield 81%). m.p. 74.0~75.5° C.

Having described our invention as related to the present embodiments, it is our intention that the invention not be limited by any of the details of the description, unless otherwise specified, but rather be construed broadly within its spirit and scope as set out in the accompanying claims.

What we claim is:

1. A method of producing acetals, comprising reacting a compound represented by formula (I), at least one compound selected from a group consisting of a compound represented by formula (II), paraformaldehyde, and trioxane; and a compound represented by formula (III), to synthesize an acetal represented by formula (IV), wherein the reaction is carried out in the presence of an oxidizing agent and an acid;

formula (I)

$$R^1-O-\underset{\underset{O}{\|}}{C}-\underset{\underset{R^2}{|}}{N}-H$$

wherein $R^1$ represents an alkyl group, an aryl group, or a heterocyclic group; and $R^2$ represents an alkyl group or an aryl group;

formula (II)

$$R^3\underset{\underset{O}{\|}}{\diagdown}R^4$$

wherein $R^3$ and $R^4$ each independently represent a hydrogen atom, an alkyl group, an alkenyl group, an alkynyl group, an alkoxycarbonyl group, an aryloxycarbonyl group, a carbamoyl group, a sulfamoyl group, an aryl group, or a heterocyclic group;

formula (III)

$$MS-C\overset{N\cdots}{\underset{X_1}{\diagup}}$$

wherein $X_1$ represents a group of non-metal atoms necessary to form a 5- or 6-membered nitrogen-containing heterocycle; and M represents a hydrogen atom or a cation;

formula (IV)

wherein $R^1$, $R^2$, $R^3$, and $R^4$ each have the same meanings as in formulae (I) and (II), and $X_2$ represents the same group of atoms as $X_1$ in formula (III).

2. The method of producing acetals as claimed in claim 1, wherein $R^1$ is represented by formula (VI):

formula (VI)

(naphthol with OH, CONHAr, and methyl substituents)

wherein Ar represents a substituted or unsubstituted alkyl group or aryl group.

3. The method of producing acetals as claimed in claim 1, wherein the oxidizing agent is a peroxide.

4. The method of producing acetals as claimed in claim 1, wherein the oxidizing agent is a hydrogen peroxide, or an addition product thereof.

5. The method of producing acetals as claimed in claim 1, wherein the acid is a proton acid.

6. The method of producing acetals as claimed in claim 5, wherein the proton acid is a hydrobromic acid.

7. The method of producing acetals as claimed in claim 1, wherein, in formulae (II) and (IV), $R^3$ and $R^4$ each are a hydrogen atom.

8. The method of producing acetals as claimed in claim 1, wherein a reaction solvent is used in the reaction, and is toluene, hexane, or a mixture thereof.

9. The method of producing acetals as claimed in claim 8, wherein the reaction solvent is a mixture of toluene and hexane with a mixing ratio of toluene/hexane being 1/1 to 1/4 by volume.

* * * * *